United States Patent
Liu et al.

(10) Patent No.: US 10,234,397 B2
(45) Date of Patent: Mar. 19, 2019

(54) MONOHYDROXYPHENYL METABOLITE URINE DETECTION REAGENT AND PREPARATION METHOD THEREOF

(71) Applicant: JIANGSU DONGBO BIO-PHARMACEUTICAL CO., LTD., Jiangsu (CN)

(72) Inventors: Dong Liu, Jiangsu (CN); Lei Li, Jiangsu (CN); Mingbin Zheng, Jiangsu (CN)

(73) Assignee: JIANGSU DONGBO BIO-PHARMACEUTICAL CO. LTD., Jiangsu (CN)

( * ) Notice: Subject to any disclaimer, the term of this patent is extended or adjusted under 35 U.S.C. 154(b) by 75 days.

(21) Appl. No.: 15/538,782

(22) PCT Filed: Oct. 23, 2015

(86) PCT No.: PCT/CN2015/092615
§ 371 (c)(1),
(2) Date: Jun. 22, 2017

(87) PCT Pub. No.: WO2016/101691
PCT Pub. Date: Jun. 30, 2016

(65) Prior Publication Data
US 2017/0370853 A1    Dec. 28, 2017

(30) Foreign Application Priority Data
Dec. 25, 2014   (CN) .......................... 2014 1 0828096

(51) Int. Cl.
| | | |
|---|---|---|
| *G01N 21/82* | (2006.01) | |
| *G01N 21/78* | (2006.01) | |
| *G01N 33/493* | (2006.01) | |
| *G01N 33/539* | (2006.01) | |
| *G01N 33/574* | (2006.01) | |

(52) U.S. Cl.
CPC ............. *G01N 21/82* (2013.01); *G01N 21/78* (2013.01); *G01N 33/493* (2013.01); *G01N 33/539* (2013.01); *G01N 33/574* (2013.01)

(58) Field of Classification Search
CPC ...... G01N 21/78; G01N 21/82; G01N 33/493; G01N 33/539; G01N 33/574
USPC ..... 436/86, 90, 96, 111, 131, 140, 164, 166, 436/174; 252/408.1
See application file for complete search history.

(56) References Cited

U.S. PATENT DOCUMENTS

| | | | | |
|---|---|---|---|---|
| 5,066,601 A | * | 11/1991 | Kweon ................. | G01N 33/52 436/63 |
| 5,094,836 A | * | 3/1992 | Kim ...................... | G01N 31/22 424/644 |
| 5,270,215 A | * | 12/1993 | Pincus .................. | G01N 33/52 356/319 |
| 2018/0031544 A1 | * | 2/2018 | Chisholm ............ | G01N 33/574 |

FOREIGN PATENT DOCUMENTS

| | | | |
|---|---|---|---|
| CN | 102004103 | * | 2/2012 |
| CN | 104390974 | * | 3/2015 |
| CN | 104390975 | * | 3/2015 |
| EP | 341803 | * | 11/1989 |

* cited by examiner

*Primary Examiner* — Maureen Wallenhorst
(74) *Attorney, Agent, or Firm* — Murtha Cullina LLP

(57) ABSTRACT

A reagent for detection of urine monophenolic metabolites and a method for preparing the reagent are disclosed, in which the monophenolic metabolites, for example, tyrosine, p-hydroxyphenyl alanine, tryptophan and 5-hydroxyindoleacetic acid can serve as tumor markers. The reagent for detection of urine monophenolic metabolites is an aqueous solution containing nitric acid, sulfuric acid, mercuric sulfate, mercurous nitrate, nickel nitrate, phosphomolybdic acid and cobalt sulfate. The preparation method includes preparation of solutions A, B, C, D and E, and mixing. The subject matter allows easy availability of raw materials, low cost, a simple preparation process, obtainment of reagents with stable performance which offer the advantages including high versatility, high sensitivity and good specificity when used in cancer detection, a simple detection process, a short detection cycle and easy determination, and is particularly suitable for large population screening, assistance in clinical cancer diagnosis and dynamic follow-up.

8 Claims, No Drawings

MONOHYDROXYPHENYL METABOLITE URINE DETECTION REAGENT AND PREPARATION METHOD THEREOF

TECHNICAL FIELD

The present invention pertains to a urinalysis reagent and, in particular relates to a reagent for detection of urine monophenolic metabolites and a method for preparing the reagent, in which the monophenolic metabolites, for example, tyrosine, p-hydroxyphenyl alanine, tryptophan and 5-hydroxyindoleacetic acid can serve as tumor markers.

BACKGROUND

Early diagnosis and early treatment of tumors is critical to improving tumor cure rates. The existing diagnostic means commonly used in clinical practices include chest X-ray, B-scan, CT, nuclear magnetic resonance (NMR), etc. and are often accompanied by procedures such as punctures and blood draws that make the patient suffer more and even may cause cross-infections. Moreover, these means cost much, and more importantly, tumors that can be detected by these means are mostly advanced tumors, leading to great pain and economic burden on the patient. Therefore, it is imperative to develop a detection method allowing easy and quick operation, low cost, high sensitivity and good repeatability.

The abnormal nucleotide metabolism in cancer cells produces monophenolic metabolites, specifically, tyrosine, p-hydroxyphenyl alanine, tryptophan and 5-hydroxyindoleacetic acid, present at contents much higher than those in normal individuals. These substances can be discharged through the urine and analysis of the contents of the monophenolic metabolites enables the inference of presence of cancer in the body. This allows early tumor detection and saves lives without adding expenses or causing the patient's fear and pain. However, some trace components or substances resulting from metabolic abnormalities caused by other diseases in the urine are also associated with mercuric and mercurous ions in the detection reagents to result in precipitates with colors, which may significantly affect the accuracy of the test results. Therefore, although the existing reagents for detection of urine metabolites are highly sensitive, they are associated with the false positive issue which significantly reduces the detection accuracy, leads to misdiagnosis and limits their application.

SUMMARY OF THE INVENTION

The present invention provides a reagent for detection of urine monophenolic metabolites and a method for preparation thereof to address the low detection accuracy issue.

In order to solve the technical problem defined above, the subject matter of the present invention is that: the reagent for detection of urine monophenolic metabolites is an aqueous solution including nitric acid, sulfuric acid, mercuric sulfate, mercurous nitrate, nickel nitrate, phosphomolybdic acid and cobalt sulfate.

Further, in the aqueous solution, the mercuric sulfate may be present in a concentration of 0.4-2.1 mol/L, with the mercurous nitrate in a concentration of 0.3-0.9 mol/L, the nickel nitrate in a concentration of 0.01-0.06 mol/L, the phosphomolybdic acid in a concentration of 3.2-14.1 mmol/L and the cobalt sulfate in a concentration of 0.1-0.4 mol/L.

Cells in precancerous lesions and in tumors in early-, middle- and late-stage cancer patients undergo abnormal proliferation which can induce a series of stress reactions, increasing the metabolism of monophenolic substances and causing the contents of urine monophenolic metabolites far higher than those in normal individuals. Monophenolic metabolites are a family of small molecules and refer specifically to tyrosine, p-hydroxyphenyl alanine, tryptophan and 5-hydroxyindoleacetic acid. As final metabolites, they are relatively stable. The present invention takes advantage of the nature of mercurous ions contained in the reagent to react with monophenolic substances to produce red and reddish precipitates. Test results show that mercurous ions contained in the aqueous solution can react with the monophenolic metabolites to result in precipitates with good colors, from the strength of which, it is possible to make an initial qualitative determination of whether a patient is likely to carry cancer cells. Additionally, the suitable concentrations of the mercuric sulfate and nickel nitrate allow these substances to react with other anions in the urine (e.g., halogen ions, nitrite ions) to result in white complex precipitates, thereby effectively circumventing the interference with the anions. If the phosphomolybdic acid is present in an excessively low concentration, then it would be incapable of effectively reacting with alkaloids in the urine, and incapable of avoiding the interference with the alkaloids, so that a false positive result of the reagent will be obtained; however, if its concentration is excessively high, it then may react with cations in the solution, for example, mercuric and mercurous ions, making them unable to react with the corresponding substances, so that a false negative result may be obtained and the specificity of the detection reagent may be increased. Further, as cobalt sulfate appears red when in the form of a solution, if the added cobalt sulfate is present in an excessively high concentration, it may mask the colors of the products from the reaction of the reagent with the urine, leading to interference as well as a false positive result. On contrary, if its concentration is too low, it cannot react with the monophenolic substances in a satisfactory way, and more importantly, mercuric and mercurous ions are susceptible to hydrolyzation, in particular when exposed to great temperature changes, if the cobalt ions are present in a low concentration, it would not be able to effectively stabilize the hydrolyzation of mercuric and mercurous ions.

The present invention also provides a method for preparing the reagent for detection of urine monophenolic metabolites, including the steps of:
1) preparation of a solution A: weighing mercuric sulfate and dissolving it in a 3 mol/L aqueous solution of sulfuric acid to obtain the solution A;
2) preparation of a solution B: weighing mercurous nitrate and dissolving it in a 4 mol/L aqueous solution of nitric acid to obtain the solution B;
3) preparation of a solution C: weighing nickel nitrate and dissolving it in double-distilled water to obtain the solution C;
4) preparation of a solution D: weighing phosphomolybdic acid and dissolving it in double-distilled water to obtain the solution D;
5) preparation of a solution E: weighing cobalt sulfate and dissolving it in double-distilled water to obtain the solution E; and
6) mixing: mixing the solutions A, B, C, D and E prepared in steps 1), 2), 3), 4) and 5) in a ratio by volume of 1:(1-1.6):(0.1-0.7):(0.2-0.3):(0.7-1.5) to obtain the reagent for detection of urine monophenolic metabolites.

Preferably, the solution A includes a mercuric sulfate content of 0.5-2 g/ml.

Preferably, the solution B includes a mercurous nitrate content of 0.6-1.5 g/ml.

Preferably, the solution C includes a nickel nitrate content of 0.1-0.3 g/ml.

Preferably, the solution D includes a phosphomolybdic acid content of 0.1-0.3 g/ml.

Preferably, the solution E includes a cobalt sulfate content of 0.1-0.5 g/ml.

The subject matter of the present invention allows easy availability of raw materials, low cost, a simple preparation process, obtainment of reagents with stable performance which offer the advantages such as high versatility, high sensitivity and good specificity when used in cancer detection, a simple detection process, a short detection cycle and easy determination, and is particularly suitable for large population screening and assistance in clinical cancer diagnosis and dynamic follow-up.

DETAILED DESCRIPTION

All the raw materials used were ordinary analytical-grade chemical reagents, and all the preparation processes were conducted at room temperature and atmospheric pressure.

EXAMPLE 1

A reagent for detection of urine monophenolic metabolites was an aqueous solution including nitric acid, sulfuric acid, mercuric sulfate, mercurous nitrate, nickel nitrate, phosphomolybdic acid and cobalt sulfate, wherein the mercuric sulfate was present in a concentration of 0.67 mol/L, with the mercurous nitrate in a concentration of 0.36 mol/L, the nickel nitrate in a concentration of 0.14 mol/L, the phosphomolybdic acid in a concentration of 6.4 mmol/L and the cobalt sulfate in a concentration of 0.10 mol/L.

It was prepared by a process including:
1) preparation of a solution A: weighing an appropriate amount of mercuric sulfate and dissolving it in a 3 mol/L aqueous solution of sulfuric acid to obtain the solution A in which the mercuric sulfate was present in a concentration of 1 g/ml;
2) preparation of a solution B: weighing an appropriate amount of mercurous nitrate and dissolving it in a 4 mol/L aqueous solution of nitric acid to obtain the solution B in which the mercurous nitrate was present in a concentration of 0.6 g/ml;
3) preparation of a solution C: weighing an appropriate amount of nickel nitrate and dissolving it in double-distilled water to obtain the solution C in which the nickel nitrate was present in a concentration of 0.3 g/ml;
4) preparation of a solution D: weighing an appropriate amount of phosphomolybdic acid and dissolving it in double-distilled water to obtain the solution D in which the phosphomolybdic acid was present in a concentration of 0.2 g/ml;
5) preparation of a solution E: weighing an appropriate amount of cobalt sulfate and dissolving it in double-distilled water to obtain the solution E in which the cobalt sulfate was present in a concentration of 0.1 g/ml; and 6) mixing: mixing the solutions A, B, C, D and E prepared in steps 1), 2), 3), 4) and 5) in a ratio by volume of 1:1.6:0.7:0.3:1.5 to obtain the reagent for detection of urine monophenolic metabolites.

EXAMPLE 2

A reagent for detection of urine monophenolic metabolites was an aqueous solution including nitric acid, sulfuric acid, mercuric sulfate, mercurous nitrate, nickel nitrate, phosphomolybdic acid and cobalt sulfate, wherein the mercuric sulfate was present in a concentration of 2.0 mol/L, with the mercurous nitrate in a concentration of 0.8 mol/L, the nickel nitrate in a concentration of 0.01 mol/L, the phosphomolybdic acid in a concentration of 3.2 mmol/L and the cobalt sulfate in a concentration of 0.37 mol/L.

It was prepared using a process including:
1) preparation of a solution A: weighing an appropriate amount of mercuric sulfate and dissolving it in a 3 mol/L aqueous solution of sulfuric acid to obtain the solution A in which the mercuric sulfate was present in a concentration of 2 g/ml;
2) preparation of a solution B: weighing an appropriate amount of mercurous nitrate and dissolving it in a 4 mol/L aqueous solution of nitric acid to obtain the solution B in which the mercurous nitrate was present in a concentration of 1 g/ml;
3) preparation of a solution C: weighing an appropriate amount of nickel nitrate and dissolving it in double-distilled water to obtain the solution C in which the nickel nitrate was present in a concentration of 0.1 g/ml;
4) preparation of a solution D: weighing an appropriate amount of phosphomolybdic acid and dissolving it in double-distilled water to obtain the solution D in which the phosphomolybdic acid was present in a concentration of 0.1 g/ml;
5) preparation of a solution E: weighing an appropriate amount of cobalt sulfate and dissolving it in double-distilled water to obtain the solution E in which the cobalt sulfate was present in a concentration of 0.5 g/ml; and
6) mixing: mixing the solutions A, B, C, D and E prepared in steps 1), 2), 3), 4) and 5) in a ratio by volume of 1:1.4:0.1:0.2:0.7 to obtain the reagent for detection of urine monophenolic metabolites.

EXAMPLE 3

A reagent for detection of urine monophenolic metabolites was an aqueous solution including nitric acid, sulfuric acid, mercuric sulfate, mercurous nitrate, nickel nitrate, phosphomolybdic acid and cobalt sulfate, wherein the mercuric sulfate was present in a concentration of 0.47 mol/L, with the mercurous nitrate in a concentration of 0.82 mol/L, the nickel nitrate in a concentration of 0.059 mol/L, the phosphomolybdic acid in a concentration of 14 mmol/L and the cobalt sulfate in a concentration of 0.27 mol/L.

It was prepared using a process including:
1) preparation of a solution A: weighing an appropriate amount of mercuric sulfate and dissolving it in a 3 mol/L aqueous solution of sulfuric acid to obtain the solution A in which the mercuric sulfate was present in a concentration of 0.5 g/ml;
2) preparation of a solution B: weighing an appropriate amount of mercurous nitrate and dissolving it in a 4 mol/L aqueous solution of nitric acid to obtain the solution B in which the mercurous nitrate was present in a concentration of 1.5 g/ml;
3) preparation of a solution C: weighing an appropriate amount of nickel nitrate and dissolving it in double-distilled water to obtain the solution C in which the nickel nitrate was present in a concentration of 0.2 g/ml;
4) preparation of a solution D: weighing an appropriate amount of phosphomolybdic acid and dissolving it in double-distilled water to obtain the solution D in which the phosphomolybdic acid was present in a concentration of 0.3 g/ml;
5) preparation of a solution E: weighing an appropriate amount of cobalt sulfate and dissolving it in double-distilled water to obtain the solution E in which the cobalt sulfate was present in a concentration of 0.3 g/ml; and
6) mixing: mixing the solutions A, B, C, D and E prepared in steps 1), 2), 3), 4) and 5) in a ratio by volume of 1:1:0.3:0.3:0.9 to obtain the reagent for detection of urine monophenolic metabolites.

EXAMPLE 4

Comparative Example

Conducting a process including: diluting 1 part of commercially available concentrated sulfuric acid into 3 parts with water and cooling the dilution to room temperature; weighing a certain amount of mercuric sulfate and dissolving it in the dilution so that mercuric ions were present at a content of 2 mol/L; diluting 1 part of commercially available concentrated nitric acid into 3 parts with water and cooling the dilution to room temperature; weighing a certain amount of mercurous nitrate and dissolving it in the dilution so that mercurous ions were present at a content of 2.2 mol/L. A comparative detection reagent can therefore be prepared by mixing the two solutions homogeneously in a volume ratio of 1:1.2.

EXAMPLE 5

Performance Validation Tests

1. Test Subjects:
Inclusion criteria: none of the subjects included took alcohol or amino acids, hormones or other drugs one day before the tests.

1) 1,754 Twenty to eighty year old patients including equal numbers of males and females, who had been clinically diagnosed (by clinical diagnostic means) with malignancies including those of the thyroid, liver, stomach, gullet, breast, cervix, nasopharynx, etc. were included.
2) A non-tumorous benign disease group of 856 twenty to eighty year old subjects including equal numbers of males and females was included.
3) A normal healthy individual group of 2,130 twenty to eighty year old individuals including equal numbers of males and females who had been examined to meet the health criteria was included.

2. Test Method
1) In each of the following tests, one of the detection reagents prepared in Examples 1-3 was used;
2) A 3-ml fresh, clean urine sample was taken from each of the subjects and loaded in an ampoule containing 0.5 ml of the reagent. After being shaken for a while, the samples were held stationary for 3-5 minutes (and warmed in a 37° C. water bath if their temperatures were lower than 20° C.). Stable precipitates were observed even after the samples were shaken, and their colors and the results were summarized in the following Table 1.

TABLE 1

Determination Criteria for Urine Tyrosine Detection

| Detection Criterion | Symbol | Color |
|---|---|---|
| Negative | − | Light yellow or white |
| Weak positive | ± | Light red or pink |
| Positive | + | Red or reddish brown |

3. Test Results
Cancer Screening:

TABLE 2

Comparison of Urine Samples of the Groups

| Example | Group | Number of Subjects | Positive | Weak positive | Negative | Detection Rate (%) |
|---|---|---|---|---|---|---|
| 1 | Malignancy group | 1,754 | 1,033 | 709 | 12 | 99.31 |
|   | Non-tumorous benign disease group | 856 | 2 | 25 | 829 | 3.2 |
|   | Normal group | 2,130 | 3 | 6 | 2,119 | 0.42 |
| 2 | Malignancy group | 1,754 | 956 | 783 | 15 | 99.14 |
|   | Non-tumorous benign disease group | 856 | 4 | 20 | 830 | 2.8 |
|   | Normal group | 2,130 | 2 | 5 | 2,117 | 0.33 |
| 3 | Malignancy group | 1,754 | 888 | 852 | 14 | 99.20 |
|   | Non-tumorous benign disease group | 856 | 5 | 18 | 833 | 2.7 |
|   | Normal group | 2,130 | 9 | 5 | 2,116 | 0.65 |

TABLE 3

Results of Detection of Different Malignancies with Reagent of Example 1

| Cancers | Thyroid Cancer | Liver Cancer | Stomach Cancer | Esophageal cancer | Breast Cancer | Cervical Cancer | Nasopharyngeal Cancer |
|---|---|---|---|---|---|---|---|
| Number of Patients | 251 | 324 | 197 | 278 | 305 | 85 | 314 |

TABLE 3-continued

Results of Detection of Different Malignancies with Reagent of Example 1

| Cancers | Thyroid Cancer | Liver Cancer | Stomach Cancer | Esophageal cancer | Breast Cancer | Cervical Cancer | Nasopharyngeal Cancer |
|---|---|---|---|---|---|---|---|
| Number of Positive Results | 251 | 324 | 195 | 276 | 301 | 85 | 312 |
| Positive Rate | 100% | 100% | 98.9% | 99.3% | 98.6% | 100% | 99.4% |

As shown above, among the 1,754 patients with malignancies from a hospital, 1,742 were detected to be positive, accounting for a detection rate of up to 99.31%. The detection rates for the normal group (0.42%) and non-tumorous benign disease group (3.2%) were both lower than 5%, demonstrating high malignancy screening sensitivity and high positive rates of the reagents for detection of urine tumor markers provided by the present invention. The results shown in Table 3 also proved that the reagents could be extensively used for identification of different malignancies.

EXAMPLE 6

The comparative reagent prepared in Example 4 was tested on the same subjects as in Example 5 and the test results were shown in Table 4.

TABLE 4

Comparison of Urine Samples of the Groups

| Group | Number of Subjects | Positive | Weak positive | Negative | Detection Rate (%) |
|---|---|---|---|---|---|
| Malignancy group | 1754 | 1023 | 591 | 140 | 92.02 |
| Non-tumorous benign disease group | 856 | 8 | 47 | 801 | 6.4 |
| Normal group | 2130 | 23 | 78 | 2029 | 4.7 |

As revealed from a comparison drawn with the comparative example, the subject matter of the present invention is capable of significantly reducing the probability of false positive results and providing high detection accuracy.

EXAMPLE 7

In order to further validate the performance of the inventive reagents, we observed dynamic changes in some of the malignant cases, i.e., their detection results before and after treatments (surgery, radiotherapy and chemotherapy), with the reagent prepared in Example 1, and the details were shown in Table 5.

TABLE 5

Urine Changes Before and After Treatments

| Cancers | Number of Patients | Before Treatments Positive | After Treatments (Surgery, Radiotherapy and Chemotherapy) | | |
|---|---|---|---|---|---|
| | | | Positive | Weak positive | Negative |
| Thyroid Cancer | 78 | 78 | 5 | 6 | 67 |
| Liver Cancer | 85 | 85 | 8 | 5 | 72 |
| Stomach Cancer | 87 | 87 | 5 | 5 | 77 |
| Esophageal cancer | 52 | 52 | 5 | 2 | 45 |
| Breast Cancer | 41 | 41 | 4 | 1 | 36 |
| Cervical Cancer | 57 | 57 | 5 | 6 | 46 |
| Nasopharyngeal Cancer | 32 | 32 | 2 | 3 | 27 |
| Lymphoma | 25 | 25 | 2 | 5 | 18 |

The above results showed that the urinalysis reagent could be used as an objective indicator for evaluating malignancy treatments (surgery, radiotherapy and chemotherapy). Similar to other tumor markers, the urine tumor markers could reflect changes in the patient's conditions and their concentrations vary with the patient's conditions. This indicates that the inventive reagents are helpful in follow-up and prognosis in cancer patients.

What is claimed is:

1. A reagent for detection of urine monophenolic metabolites, wherein the reagent is an aqueous solution comprising nitric acid, sulfuric acid, mercuric sulfate, mercurous nitrate, nickel nitrate, phosphomolybdic acid and cobalt sulfate.

2. The reagent for detection of urine monophenolic metabolites according to claim 1, wherein in the aqueous solution, the mercuric sulfate is present in a concentration of 0.4-2.1 mol/L, with the mercurous nitrate in a concentration of 0.3-0.9 mol/L, the nickel nitrate in a concentration of 0.01-0.06 mol/L, the phosphomolybdic acid in a concentration of 3.2-14.1 mmol/L and the cobalt sulfate in a concentration of 0.1-0.4 mol/L.

3. A method for preparing a reagent for detection of urine monophenolic metabolites as defined in claim 1, the method comprising the steps of:

1) preparation of a solution A: weighing and dissolving mercuric sulfate in a 3 mol/L aqueous solution of sulfuric acid to obtain the solution A;

2) preparation of a solution B: weighing and dissolving mercurous nitrate in a 4 mol/L aqueous solution of nitric acid to obtain the solution B;

3) preparation of a solution C: weighing and dissolving nickel nitrate in double-distilled water to obtain the solution C;

4) preparation of a solution D: weighing and dissolving phosphomolybdic acid in double-distilled water to obtain the solution D;

5) preparation of a solution E: weighing and dissolving cobalt sulfate in double-distilled water to obtain the solution E; and 6) mixing: mixing the solutions A, B, C, D and E prepared in steps 1), 2), 3), 4) and 5) in a ratio by volume of 1: (1-1.6): (0.1-0.7): (0.2-0.3): (0.7-1.5) to obtain the reagent for detection of urine monophenolic metabolites.

4. The method according to claim 3, wherein a content of the mercuric sulfate in the solution A is 0.5-2 g/ml.

5. The method according to claim 3, wherein a content of the mercurous nitrate in the solution B is 0.6-1.5 g/ml.

6. The method according to claim 3, wherein a content of the nickel nitrate in the solution C is 0.1-0.3 g/ml.

7. The method according to claim 3, wherein a content of the phosphomolybdic acid in the solution D is 0.1-0.3 g/ml.

8. The method according to claim 3, wherein a content of the cobalt sulfate in the solution E is 0.1-0.5 g/ml.

* * * * *